United States Patent [19]

Kuylen et al.

[11] Patent Number: 5,905,031
[45] Date of Patent: *May 18, 1999

[54] IDENTIFICATION OF BLAST CELLS IN A LEUKOCYTE CELL PREPARATION

[75] Inventors: Nazle Kuylen, Miami; Harold R. Crews; Gerald E. Jaffe, both of Pembroke Pines; Maria Barcelon, Ft. Lauderdale; Francis J. Lucas, Boca Raton; Nancy M. Garcia, Miami, all of Fla.

[73] Assignee: Coulter International Corp., Miami, Fla.

[*] Notice: This patent is subject to a terminal disclaimer.

[21] Appl. No.: 08/742,620

[22] Filed: Nov. 1, 1996

Related U.S. Application Data

[63] Continuation-in-part of application No. 08/444,051, May 18, 1995, Pat. No. 5,698,411.

[51] Int. Cl.⁶ .................................................. C12Q 1/02
[52] U.S. Cl. ................................ 435/29; 435/4; 435/34
[58] Field of Search .................................... 435/29, 4, 24, 435/25, 34, 968

[56] References Cited

U.S. PATENT DOCUMENTS

| | | | |
|---|---|---|---|
| 4,996,040 | 2/1991 | Kass | 424/3 |
| 5,106,744 | 4/1992 | Kass | 435/240.2 |
| 5,242,805 | 9/1993 | Naleway et al. | 435/18 |
| 5,698,411 | 12/1997 | Lucas et al. | 435/29 |

OTHER PUBLICATIONS

Lauria F., The Presence of Lymphoid–Associated Antigens in Adult Acute Myeloid Leukemia is Devoid of Prognostic Relevance, Stem Cells 13:428–434. 1995.
Paietta E., Detection of Terminal Transferase in Acute Myeloid Leukemia by Flow Cytometry, Cytometry 16:256–261. 1994.
Horvatinovich J., Detection of Terminal Deoxynucleotidyl Transferase by Flow Cytometry: A Three Color Method, Cytometry 18:228–230. 1994.
453 Jun. 1992 Martin et al.
Lowry, O., et al., "The Fluorometric Measurement of Pyridine Nucleotides," *J. Biol. Chem.*, 224:1047–1067 (1957).
Rotman, B., "Genetic Control of Immunologic Unresponsiveness to Adjuvant–Free Solutions of β–D–Galactosidase, "*J. Immunology*, vol. 120, No. 8, pp. 1460–1464 (1978).
De Macario, et al. "Antibody–mediated Activation of a Defective β–D–Galactosidase:Dimeric Form of the Activatable Mutant Enzyme," *PNAS USA*, vol. 75, No. 2, pp. 720–724 (1978).
Rotman, B. et al., "Antibody–Mediated Activation of a Defective β–D–Galactosidase Extracted from an *Escherichia coli* Mutant," *PNAS*, vol. 60, pp. 660–667 (1968).
Hulett, H.R., et al., "Cell Sorting: Automated Separation of Mammalian Cells as a Function of Intracellular Fluorescence," *Science*, 166:747–749 (1969).
Dolbeare, F.A. et al., "Flow Cytometric Measurement of Peptidases with Use of 5–Nitrosalicyladehyde and 4–Methoxy–β–Naphthylamine Derivatives," *Clin. Chem.* vol. 23, No. 8, 1485–1491 (1977).
Rabinovitch, P.S. et al., "Introduction to Functional Cell Assays, " *Ann. NYAS*, 667:252–264 (1990).
Valet, G. et al., "White Cell and Thrombocyte Disorders", *Ann. NYAS*, 677:233–251 (1993).
Bass, D.A. et al., "Flow Cytometric Studies of Oxidative Product Formation by Neutrophils: A Graded Response to Membrane Stimulation," *Immunology*, vol. 130, No. 4, pp. 1910–1917 (1983).
Rothe, G. et al., "Dihydrohodamine 123: A New Flow Cytometric Indicator for Respiratory Burst Activity in Neutrophil Granulocytes, " *Naturwissenschaften* 75, 354–355 (1988).
Royall, J. et al, "Evaluation of 2', 7'–Diclorofluorescin and Dihydrorhodamine 123 as Fluorescent Probes for Intracellular $H_2O_2$ in Cultured Endothelial Cells, "*Arch. Biochem. & Biophys.*, vol. 302, No. 2, 348–355 (1993).
Vowells, S.J. et al., "Flow Cytometric Analysis of the Granulocyte Respiratory Burst: A Comparison Study of Fluorescent Probes, "*J. Imm. Methods*, 178, pp. 89–97 (1995).
Duque, R. E., "Flow Cytometric Analysis of Lymphomas and Acute Leukemias", *Ann. NYAS, Clinical Flow Cytometry*, 677 pp. 309–325 (Mar. 20, 1993).
Lauria, F., et al., "The Presence of Lymphoid–Associated Antigens in Adult Acute Myeloid Leukemia is Devoid of Prognostic Relevance,"*Stem Cells*, 1995; 13:428–434.
Paietta, E., et al., "Detection of Terminal Transferase in Acute Myeloid Leukemia by Flow Cytometry,"*Cytometry*, 16:256–261 (1994).
Bass, D.L., et al., "Polymorphonuclear Leukocyte bactericidal Activity and oxidative Metabolism during glutathione Peoxidase Deficiency,"*Infection & Immunity*, vol. 18, No. 1, pp. 78–84 (1977).

*Primary Examiner*—Ralph Gitomer
*Attorney, Agent, or Firm*—Mitchell E. Alter

[57] ABSTRACT

The necessity to detect blast cells in a patient sample to determine a treatment regime for leukemia has long been desired. The present invention relates to a method and assay reagents for identification of blast cells in a fluid sample. The method further enables the determination of the lineage of the blast cells. The new method provides a determination of blast cells in less time than prior art methods.

34 Claims, 5 Drawing Sheets

| FIG. 1A | FIG. 1B | FIG. 1C | FIG. 1D |
|---|---|---|---|
| SAMPLE (Leukocytes) | SAMPLE (Leukocytes) | SAMPLE (Platelets, RBCs & Leukocytes) | SAMPLE (Platelets or RBCs or Lymph, Mono, Gran) |
|  |  |  |  |
| WASH 4X >10,000:1 | LYSE UNWANTED CELLS | WASH 4X | MECHANICAL SEPARATION OF CELL POPULATION |
|  |  |  |  |
| ADD REAGENT INCUBATE | WASH 4X | ADD REAGENT INCUBATE | WASH 4X |
|  |  |  |  |
| LYSE UNWANTED CELLS | ADD REAGENT INCUBATE | DATA COLLECTION | ADD REAGENT INCUBATE |
|  |  |  |  |
| DATA COLLECTION | DATA COLLECTION | RESULT | DATA COLLECTION |
|  |  | |  |
| RESULT | RESULT | | RESULT |

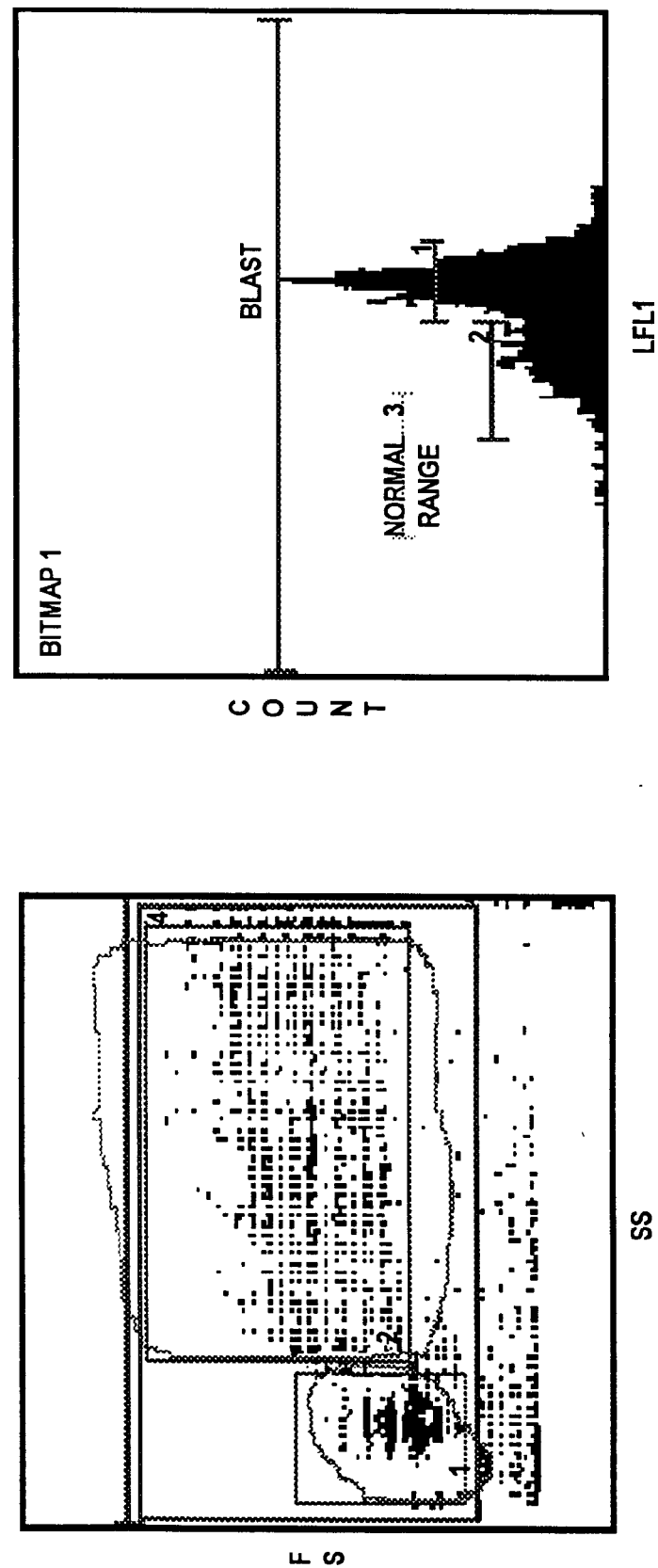

Not Bimodal

Not Myeloblast

Bimodal Lymphocytic
Assay Reagent - 38% Blasts       Manual - 4% Blasts
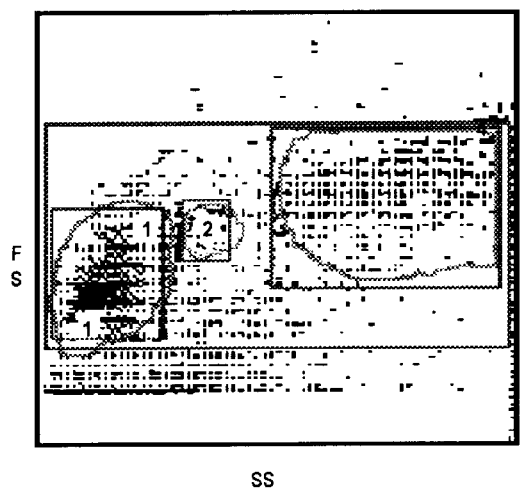
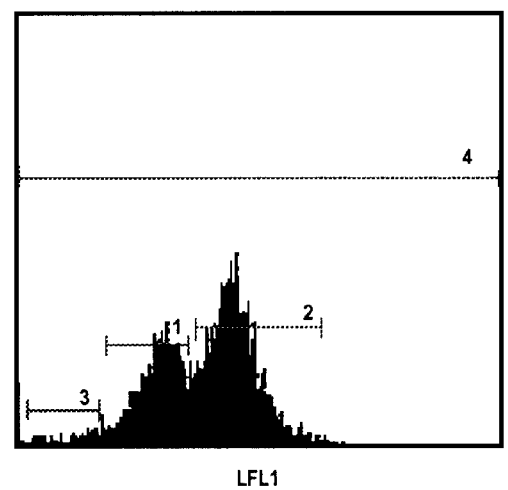
FIG. 5A                          FIG. 5B

IDENTIFICATION OF BLAST CELLS IN A LEUKOCYTE CELL PREPARATION

CROSS REFERENCE TO RELATED APPLICATION

This application is a continuation-in-part of patent application Ser. No. 08/444,051, filed May 18, 1995 now U.S. Pat. No. 5,698,411.

BACKGROUND OF THE INVENTION

Cellular enzymes are a key to metabolic diversity, differentiation and cytopathology among cells. However, cellular enzymes are extremely diverse. Their functions include host defense, transport of molecules through membranes, production of energy and synthesis of the cellular constituents. As many as a thousand different enzymes might be operative in any given cell, but only a few dozen may define the function of any one cell type. In addition, enzyme levels can vary by factors of tens to hundreds, depending on the functional or differential state of the cell. Furthermore, these same enzymes may be non-detectable in quiescent cells of the same functional phenotype and cells performing different functions.

Morphologic classification of chemical constituents within cells was aided by the use of cytochemical stains. These methods used were enzymatic techniques and in general, all prior art assays for enzymatic activity have been cytochemical colorimetric assays. Examples of the prior art measurement of enzyme activity are:

1) Acetate esterase activity measured with α-Napthyl acetate has been used together with other esterase activities to identify leukocyte cell types and is generally high in normal monocytes and megakaryocytes and in blast cells of acute myelomonocytic leukemia, acute monocytic leukemia and acute erythroleukemia.

2) Cloroacetate esterase activity measured with Naphthol-AS-D chloroacetate is generally high in normal promyelocytes and neutrophils and in blast cells of acute myeloblastic leukemia with maturation, acute promyelocytic leukemia and acute myelomonocytic leukemia.

3) Butyryl esterase activity measured with α-Napthyl butyrate has been used to identify different cell types and is generally high in normal monocytes and in blast cells of acute myelomonocytic leukemia and acute monocytic leukemia. Butyryl fluorescein is also a substrate for phospholipase $A_2$, an early enzyme in the biochemical cascade leading to the production of prostaglandins and leukotrienes.

4) Assays of acid phosphatase activity have been used together with assays of esterase activity to identify many different cell types. Monocytes, neutrophils and T-lymphocytes have relatively high acid phosphatase activity while B-lymphocytes have relatively low acid phosphatase activity. In addition, blast cells of acute promyelocytic leukemia and acute myelomonocytic leukemia have been shown to have relatively high acid phosphatase activity.

5) A derivative of β-glucuronidase has been used to measure degranulation in polymorphonuclear lymphocytes (PMN) in a test of the ability of different non-steroidal anti-inflammatory drugs (NSAIDS) to inhibit PMN functions. Peripheral blood T-lymphocytes display higher β-glucuronidase activity that peripheral blood B-lymphocytes. Fluorescein di-glucuronide is a negatively charged compound. To help other derivatives of sugars pass through cell membranes in assays of β-glucosidase, a lysomotropic detergent (N-dodecylimidazole) was used.

The study of enzymes by flow cytometry may have had its beginnings in 1957 when Lowry (*J. Bio. Chem.*, 224:1047–1067 (1957)) studied dehydrogenases by fluorescence microscopy in cells using NADP. Rotman, (*J. Immunology*, Vol. 120, No. 8, pp. 1460–1464 (1978); PNAS USA, Vol. 75, No. 2, pp. 720–724 (1978); and *PNAS*, Vol. 60, pp. 660–667 (1968)) studied β-galactosidase in ribosomes. In 1969, Hulett (Science, 166:747–749 (1969)) prepared esterase compounds with fluorescein. Naphthylamine, naphthol and coumarin derivatives were studied by Dolbeare and Smith (*Clin. Chem.* 23/8,1485–1491 (1977)). Functional cell assays for ionized calcium, intracellular pH, glutathione and membrane potential were studied by Rabinovitch (*NYAS*, 667:252 (1990) and Valet (*NYAS*, 677:233 (1993)) described phagocytosis, respiratory burst, activation antigens and protease activity in leukocytes.

Dichlorofluorescin diacetate (2', 7' dicholorofluorescin diacetate hereinafter referred to as DCFH-DA) as a cellular substrate for oxidative burst was first suggested by Bass, et. al. *J. Immunology*, Vol. 130, No. 4, pp. 1910–1917 (1983). It is sensitive to the oxygen radical. The use of DCFH-DA was used to determine oxidative burst resulting from peroxidase or catalase in neutrophil cells. The concept was that a reaction with DCGFH-DA provided a functional test of a neutrophil cell to determine whether or not there was enough oxygen radical to neutralize bacteria. Therefore, the test of neutrophil functionality was to determine its efficacy in fighting disease.

Bass et al. *J. Immunology*, Vol. 130, No. 4, pp. 1910–1917 (1983), first monitored the oxidative burst in neutrophils using DCFH-DA in 1983. Bass et al. proposed that the conversion of non-fluorescent dichlorofluorescin diacetate (DCFH-DA) to the highly fluorescent compound 2',7'-dichlorofluorescein (DCF) happens in several steps. First, DCFH-DA is transported across the ceil membrane and deacetylated by esterases to form the non-fluorescent compound 2',7'-dichloroflluorescin (DCFH). This compound is trapped inside cells. Next, DCFH is converted to DCF through the action of peroxide ($H_2O_2$).

$$\text{DCFH—DA} \xrightarrow{\text{esterases}} \text{DCFH} \xrightarrow{H_2O_2} \text{DCF}$$

Measurement of the fluorescence of the DCF is therefore a measure of the production of $H_2O_2$.

The contribution of peroxidase to the oxidation of DCFH is unknown. In solution, the oxidation of DCFH is markedly increased by peroxidase. However, azide, which is an inhibitor of myeloperoxidase, also increases intracellular oxidation of DCFH. Bass et al. hypothesize that this increase may be due to azide-mediated inhibition of catalase, an enzyme that competes with DCFH for interaction with peroxide generated by the cell.

Rothe, Oser and Valet, Naturwissenschaften, 75, 354–355 (1988), introduced dihydrorhodamine 123 (DHR 123) as a flow cytometric indicator for oxidative burst activity in neutrophils in 1988 as a more sensitive probe of oxidative burst activity than DCFH-DA. Rothe, Oser and Valet found that DHR 123 could detect the relatively small oxidative burst increase produced by stimuli such as the chemotactic peptide f-Met-Leu-Phe; this increase was only barely measurable with DCFH-DA.

Both DCFH-DA and DHR 123 are used to measure products of the oxidative burst of polymorphonuclear leukocytes. During the oxidative burst, cellular enzymes NADPH oxidase and superoxide dismutase produce the superoxide anion ($O_2^-$) and hydrogen peroxide ($H_2O_2$) in the following reactions:

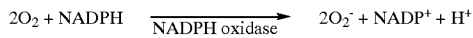

$$2O_2 + NADPH \xrightarrow{NADPH\ oxidase} 2O_2^- + NADP^+ + H^+$$

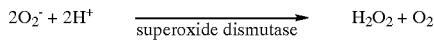

$$2O_2^- + 2H^+ \xrightarrow{superoxide\ dismutase} H_2O_2 + O_2$$

When myeloperoxidase is present, it breaks down the hydrogen peroxide:

$$H_2O_2 + X^- \xrightarrow{myeloperoxidase} OX^- + H_2O \quad :X^- = Cl^-, Br^-, or\ I$$

Royall and Ischiropoulos *Arch. Biochem. & Biophys.*, Vol. 302, No. 2, pp. 348–355 (1993), did several experiments on the permeability of the cell membranes of cultured endothelial cells to DCFH-DA, DCFH, and DCF. In their experiments, Royall and Ischiropoulos incubated cells in media containing DCFH-DA and then washed the cells into media without DCFH-DA. They then measured the intracellular and extracellular concentrations of DCFH-DA, DCFH, and DCF. They found that there was a greater than 90% loss of DCFH and DCF from the cells after one hour, demonstrating that DCFH and DCF are not trapped within the endothelial cells.

In their experiments on the diffusion of the probes across the cell membranes, Royall and Ischiropoulos found that intracellular DHR 123 concentrations, like DCFH and DCF concentrations, decreased by 90% after the cells were incubated for one hour in media that did not contain DHR 123. However, the product of the reaction, intracellular rhodamine 123, decreased by only 15% after 1 hour. Therefore, the rhodamine 123 was found to be retained by the cell better than DCF.

In their experiments on the sensitivity of the probes, Vowells, *J. Imm. Methods*, 178, pp. 89–97 (1995), et al. found that the fluorescent signal measured in normal granulocytes stimulated with PMA was seven times higher for DHR 123 than DCFH-DA. The addition of 0.017% azide increased the signal from DCFH-DA by 140% and the signal from DHR 123 by 25%. Vowells et al. also studied mixtures of normal granulocytes and granulocytes from patients with chronic granulomatous disease (CGD), a rare genetic disorder caused by defects in the NADRH oxidase enzyme complex. Vowells et al. found that DHR 123, but not DCFH-DA, could detect normal sub-populations as small as 0.1% in mixtures of normal/CGD granulocytes.

The necessity to detect blast cells in a patient sample to determine a treatment regime for leukemia has long been desired. Consequently, to determine blast accurately, one uses a Wright stain, which is a classical staining technique to confirm the presence of blast cells and identifies cells by their lipid protein and nucleic acid concentrations. Then, one employs a colorimetric peroxidase stain on a microscope slide preparation to indicate the presence or absence of the peroxidase in the blast cell. A panel of cytochemical stains are employed to microscopically identify these malignant cell types. The use of these specific staining techniques can then establish the cell line involved. In these techniques, the cells are not metabolically active.

Over the years, the microscopic examination of leukocytes, erythrocytes and platelets on a blood film, known as the manual differential count, has been recognized as the foundation for diagnosis of hematological abnormalities. However, the manual method has the reputation of being expensive and tedious, requiring a highly skilled technologist and having a relatively high inherent error rate. The manual method's high variability is related to the preparation techniques, sample size, and operator subjectivity.

In addition, acute leukemia patients are often treated with drugs which have effects upon bone marrow cell production roles and which can alter the morphology of blood cells, making it difficult to correctly identify these cells. Results are based on subjective interpretations.

Clinical practice would prefer determining blast cells at less than 1%. Early detection is most preferable because treatments, consisting of chemotherapy and other harsh treatments which kills normal cells as well as abnormal cells, could be administered to minimize the adverse consequences of the treatment and a lower detection level will also enable the monitoring the efficacy of drug therapies.

SUMMARY OF THE INVENTION

The present invention relates to a method for identification of blast cells in a fluid sample comprising taking a body fluid sample from an individual, said sample containing metabolically active cells; using said fluid sample to prepare at least one test sample, said test sample containing metabolically active cells; adding an assay reagent to each prepared test sample, said assay reagent containing a fluorogenic indicator group being selected for its ability to have a non-fluorescent first state before said assay reagent reacts with an enzyme within said cells, and a fluorescent second state excitable at a wavelength above 450 nm after said assay reagent reacts with said enzyme within said cell, said assay reagent having a fluorescence less than the auto-fluorescence of a metabolically active cell before reacting with said enzyme within said cell; detecting fluorescence and two channels of light scattering for the cels in said test sample in an instrument capable of such detecting; and analyzing said fluorescence product and said light scattering of said cells to identify blast ceDs contained is said sample.

The present invention also relates to a method wherein a fluid sample is used to prepare at least two test samples, wherein a first test sample is added to a first assay reagent which reacts with oxidoreductase enzymes, and a second test sample is added to an assay reagent which reacts with an esterase enzyme.

The present invention also relates to a method wherein a fluid sample is used to prepare at least three test samples, wherein a first test sample is added to a first assay reagent which reacts with oxidoreductase enzymes, a second test sample is added to a second assay reagent which reacts with an esterase enzyme, a third test sample is added to a third assay reagent which reacts with a phosphatase enzyme and a fourth test sample is added to a fourth assay reagent which reacts with a glucuronidase enzyme.

The present invention further relates to a method wherein a fluid sample is used to prepare at least four test samples, wherein a first test sample is added to a first assay reagent which reacts with oxidoreductase enzymes, a second test sample is added to a second assay reagent which reacts with an esterase enzyme, a third test sample is added to a third assay reagent which reacts with a phosphatase enzyme and a fourth test sample is added to a fourth assay reagent which reacts with a glucuronidase enzyme.

The present invention also relates to an assay reagent for the identification of blast cells in a fluid sample by the measurements of cellular enzyme activity comprising an assay compound selected from 3', 6' fluorescein dichloroacetate and 3', 6' fluorescein dibutyrate; a physiological buffer; wherein said assay reagent has a purity less than the autofluores-cence of a metabolically active cell and a pH from 4 to 7.5. Preferably, the assay reagent is lyophilized.

BRIEF DESCRIPTION OF THE DRAWINGS

There are shown in the drawings embodiments which are presently preferred, it being understood, however, that the invention is not limited to the precise instrumentalities and arrangements shown, wherein:

FIGS. 1A, 1B, 1C and 1D are flow charts of four assay protocols according to the invention;

FIGS. 3A and 3B depict histograms which illustrate the use of an assay reagent according to this invention to provide an indication of myeloblast cells.

FIGS. 5A and 5B depict histograms of lymphocytes, monocytes, granulocytes and blast cells which illustrates the use of an assay reagent according to this invention to provide an indication that the blast cells are lymphocytc cells.

DETAILED DESCRIPTION OF THE PREFERRED EMBODIMENTS

Figure 2:
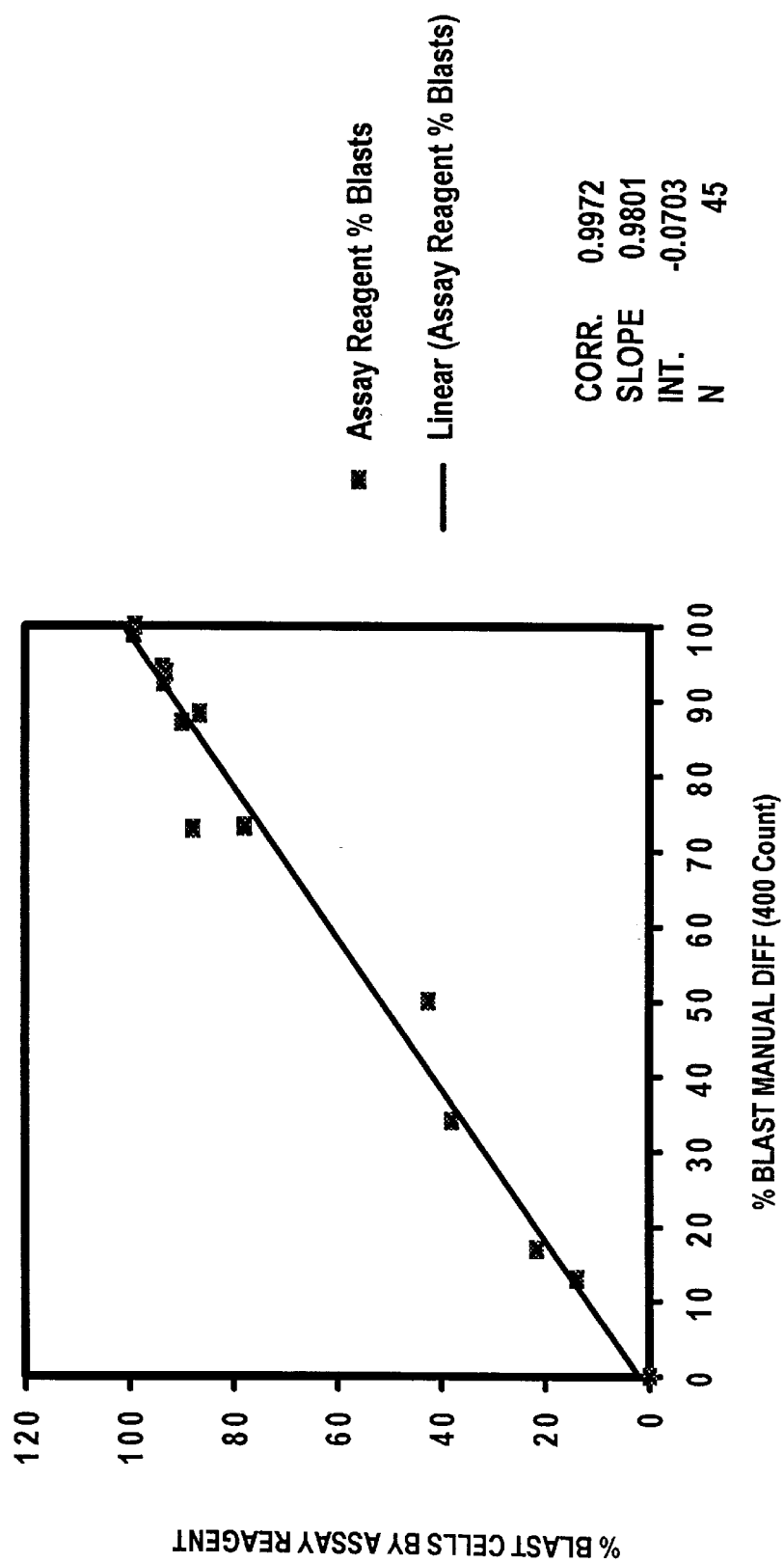
FIG. 2 depicts a correlation of the determination of percent blast cells obtained by flow cytometry using the method of this invention compared to percent blast cells obtained by the Wright stain method.

The following outline will be used to describe the preferred embodiments of this invention:
I. Types of Assays
II. Preparation of Metabolically Active Whole Cells
III. Assay Compound
IV. Preparation Of An Assay Reage nt Which Contains An Assay Compound
V. Assay Conditions
VI. Assay Protocol
VII. Data Analysis
I. Types of Assays It has been discovered that an assay reagent can be used in a method to determine enzymatic activity of metabolically active whole cells to provide indication of the presence of a disease, the progress of a disease, the efficacy of a drug, and cell differentiation. More specifically, changes in the activity of one or more enzymes can be examined to provide an indication of the presence and progress of a disease such as leukemia. In addition, the measurement of the activity of enzymes can provide an indication of the response to certain drugs or treatments, since the activity of the enzymes will change if the drug is successfully fighting, modulating or treating the disease. Still further, it has been determined that differentiation of leukemic cells can be determined by the presence of oxidoreductase and one or more selected enzymes.
II. Preparation of Metabolically Active Whole Cell Sample The assay reagent is reacted with a metabolically active whole cell analyte. The metabolically active whole cells are contained in tissue, blood, cell cultures or other cell containing constituents, such as in spinal fluid, peritoneal, or a tissue cell suspension, prepared from bone marrow aspirates or lymph nodes such as from a biopsy. In a preferred embodiment, the metabolically active whole cells are obtained from whole blood or bone marrow aspirates. Preferably, the metabolically active whole cells are separated into cell types. The metabolically active cells to be analyzed are isolated by known techniques such as differential lysis, differential centrifugation, and affinity columns. However, separation of the cells to be studied from other cells is not always essential.

The cells are usually washed to remove any extracellular enzymes, optionally with lysis or physical separation of unwanted cells. Several preferred techniques for accomplishing this are summarized in FIGS. 1A–1D.

The analysis of the segregated metabolically active cells provides specificity for a particular enzyme analysis. For example, when the metabolically active cell is a leukocyte blood cell, the method comprises separating the leukocyte cell from the cell analyte, washing the remaining leukocyte cell to remove any serum or plasma enzymes, contacting an assay reagent compound with the leukocyte cell, and determining fluorescence from the leukocyte cell (See FIG. 1B). A modification of this method comprises washing the cell analyte to remove any serum or plasma enzymes, contacting an assay compound with the cell analyte, separating the leukocyte blood cells from the cell analyte, and determining fluorescence from the leukocyte cells (See FIG. 1A). In addition, another method that can be used for cell analytes of leukocyte blood cells, nucleated erythrocyte blood cells and platelets analytes comprises washing the cell analyte to remove any serum or plasma enzymes, contacting an assay compound with the analyte and determining fluorescence from the analyte (See FIG. 1C).

To confirm that cells are metabolically active at the time of the assay, it is desirable that the viability of the cells be checked at the time of the assay. Several tests are useful to determine the viability of cells. Trypan blue is a blue stain which diffuses into the cell and is removed by cells if the cells are viable. Dead cells will not remove the dye and will take on a blue color. Propidium iodide is a DNA-RNA stain which, if the cell is dead and membranes are damaged, will penetrate the cell and stain the DNA-RNA. Fluorescein diacetate-propidium iodide will cause living cells to fluoresce a green color because the fluorescein diacetate will be hydrolyzed, while dead cells will fluoresce a red color from the propidium iodide. Mature red blood cells do not undergo cell division, and therefore a test for the presence of 2,3-diphosphoglucose dehydrogenase (which is an indicator of cell division) is a useful test for viability.

The assay of the present invention is particularly useful for measuring intracellular concentrations of enzymes in mammalian cells such as human cells. However, the assay should also be useful in various or other types of cells which have metabolic activity.
III. Assay Compound According to the present invention, an assay reagent is manufactured for determining the activity of an enzyme in a metabolically active whole cell. The assay reagent must be compatible with the cell such that the cell will remain metabolically active for at least the duration of the assay. The assay reagent comprises at least one assay compound which is capable of passing through the cell wall. The assay compound must be small enough that it can be transmitted into the cell. An assay compound having a molecular weight of less than about 5,000 is presently preferred.

The assay compound will have a first state before reacting with an enzyme contained in the metabolically active whole cell, and a second state when it has reacted with the enzyme within the cell. After reacting with the enzyme, the assay compound is excitable (caused to fluoresce) at a wavelength about the visible range, for example, preferably at a wavelength between about 450 to 500 nanometers (nm). The assay compound will usually emit in the range of about 480 to 620 nm, preferably 500 to 600 nm and more preferably 500 to 550 nm. Auto-fluorescence of the cell is most prevalent below about 500 nm. Suitable assay compounds include DCFH-DA, dihydrorhodamine 123 and nitroblue tetrazolium. These three assay compounds react with the oxidoreductase enzymes.

Preferably, the assay compound will contain a leaving group and an indicator group. The leaving group is selected for cleavage by the enzyme. The indicator group is selected for its ability to have a first state when joined to the leaving group, and a second state when the leaving group is cleaved from the indicator group by the enzyme. The indicator group is preferably derived from fluorogenic and chemiluminescent compounds. The indicator group should be quenched when joined to the leaving group. The term quenched means that the indicator group has almost no fluorescence or chemiluminescence when joined to the leaving group. When the leaving group is separated from the indicator group, the resulting indicator compound will have a fluorescence. Suitable fluorogenic indicator compounds include xanthine compounds. Preferably, the indicator compound is fluorescein.

Leaving groups for an esterase enzyme are preferably prepared by the synthesis of carboxylic acids comprising between 2 and 30 carbon atoms. The carboxylic acids can be saturated or unsaturated. The carboxylic acid preferably contains 2 to 24 carbons and more preferably 4 to 24 carbon atoms. Analogs of these carboxylic acids can also be used. The carboxylic acids can be natural or synthetic in origin. Examples are butyric, caproic, palmitic, stearic, oleic, linoleic and linolenic acid. For the present invention, the preferred leaving group would be selected from acetate and chloroacetate and butryrate.

Preferred assay compounds for esterase enzymes are selected from FDA (3', 6' fluorescein diacetate), FDClAc (3', 6' fluorescein dichloroacetate), FDB (3', 6' fluorescein dibutyrate). FDA, FDClAc and FDB are substrates for many different esterases in human tissues. It has been found that FDA (3', 6' fluorescein diacetate) when combined with sodium fluoride inhibits enzyme activity for cells of monocytic lineage. In the assay reagent, FDA-NaF, the concentration of sodium fluoride will range from approximately 300 to 1500 milligrams per liter, preferably 500 to 1,000 milligrams per liter.

Leaving groups for phosphatases are preferably prepared by the synthesis of phosphates, phosphatidic acids, phospholipids and phosphoproteins. Analogs of these compounds can also be used. Examples are ATP, ADP, AMP and cyclic AMP (c-AMP). For the present invention, the preferred leaving group would be phosphate. The preferred assay compound for phosphatases is 3', 6' fluorescein diphosphate, 4'(5') carboxy fluorescein diphenylphosphate, and fluorescein diphenylphosphate. Preferably the assay compound will be is 3', 6' fluorescein diphosphate (FDP). When using FDP, the preferred assay reagent is the is 3', 6' fluorescein diphosphate.ammonium salt (FDP-AS) which can be hydrolyzed by the enzyme acid phosphatase.

Leaving groups for saccharidases are prepared by the synthesis of carbohydrates, sugars, glycoproteins and glycolipids. The preferred assay compound for β-glucuronidase enzyme is fluorescein-β-D-diglucoronide. Fluorescein-β-D-diglucoronide is hydrolyzed by the lysosomal enzyme β-glucuronidase.

The assay compound is purified to acceptable levels for the assay. It is very important that the side reaction products, by-products and starting materials from the synthesis of the assay compound be removed which would diminish the utility of the assay. Non-physiologically acceptable impurities should be removed. In addition, the background noise generated from impurities should be less than the auto-fluorescence of a metabolically active cell.

It has been found that when impurities are present, the impurities can be an inhibitor to enzyme activity. Still further, metal impurities in any of the starting materials can poison the enzymes, prevent hydrolysis of the assay compound and interfere with the accuracy of the enzyme assay.

In addition, impurities will create background fluorescence which will add to the natural fluorescence of the cell to create a level of background noise which can interfere with the detection of enzyme generated fluorescence. Fluorescent impurities can be taken up by the cell, and a rate measurement of fluorescence against time will show a false rate of increasing fluorescence that is due only to this cellular uptake of fluorescent impurities. This is a particular problem if the assay is conducted to determine the presence or absence of an enzyme, since this impurity will indicate a rate of fluorescence which will falsely appear to be attributable to enzymatic activity.

The fluorescence impurities should be removed to a level that they do not obscure the baseline detection of the enzyme in the cell. The baseline detection can be established by analyzing log dilutions of an indicator group. Preferably the impurities should be removed so that the fluorescence of the impurities is less than the auto-fluorescence of the metabolically active cell.

Therefore, it is preferred that the impurities in the assay reagent should be removed to a concentration of less than the fluorescence generated by about $1 \times 10^{-6}$M and more preferably less than the fluorescence generated by about $1 \times 10^{-7}$ Molar free indicator group. This amounts to a 100,000 photon count using rhodamine 110 as a standard at $1 \times 10^{-7} - 10^{-8}$M, preferably $5 \times 10^{-8}$M in a 1 cm path length cuvette when measured over 10 minutes on a photon counting spectrofluorometer manufactured by the SLM Company of Chicago, Ill. This corresponds to a use level on the flow cytometer where no cellular false positive can be detected for a 10 minute period at the highest sensitivity setting. This has been found to require a concentration of impurities of less than one part per one hundred thousand, more preferably less than one part per five hundred thousand, most preferably less than one part per million.

The presence of impurities causes a decrease in the storage stability of the compound, resulting in an increased autohydrolysis which leads to increased background fluorescence. A compound should be free of impurities such that when the compound (or reagent containing the compound) is stored at 4° C. for 30 days, preferably 90 days, more preferably 180 days, most preferably one year, the background fluorescence increases less than 10%, preferably less than 5%, most preferably less than 1% over these time periods, respectively. The purified assay compound can be stored in a sealed container over dry nitrogen under atmospheric pressure or can be lyophilized and stored in a sealed vial. The starting point in time for measuring stability is usually immediately after purification of the assay compound is completed, but it can be any time such as immediately after the preparation of the assay reagent is completed.

IV. Preparation Of An Assay Reagent Which Contains An Assay Compound

The assay reagent needs to be compatible with the metabolically active cell. The assay reagent should have an osmolality of from about 250 milliosmoles to 350 milliosmoles, preferably from about 275 milliosmoles to 320 milliosmoles. Further, the pH of the assay reagent will be between about 4 and 7, preferably between about 5.0 and 6.5. It has been found that the assay compounds will autohydrolyse at pH above 7 which will decrease shelf stability, reconstituted stability of a lyophilized assay reagent, and affect the assay by giving false positives.

In addition, the efficacy of an intracellular assay is substantially improved by the addition of one or more components in the assay reagent. Examples of improvements include a reduction of reaction time, increased selectivity for the targeted enzyme, reduction of competing enzyme reactions, increasing signal of enzyme reaction, increasing reactivity of the assayed enzyme relative to other non-targeted enzymes, increasing the retention time of the indicator group within the cell and other similar advantageous results.

Additional components include buffers, cofactors, moduiators, inhibitors, activators for increasing activity of the target enzymes over other non-targeted enzymes, solubilizing components and retention components can be included in the assay reagent to improve the enzyme assay results. These components are physiologically acceptable to the metabolically active whole cell that is being assayed.

The chemical nature of the buffer is important to the reactivity of the assay compound with the cellular enzymes. Buffer components that show no inhibitory effect to the cells can be used. Suitable buffer components are N-tris (hydroxymethyl)methyl-2-aminoethanesulfonic acid (TES), Hanks Balanced Salt Solution (HBSS), 2-N-morpholinoethanesulfonic acid (MES), and HEPES. In addition, a metabolic energy source such as a sugar (glucose) can be added when using HBSS. The preferred buffer components are MES for acidic solutions.

The assay compound must be soluble in the aqueous media. Solubility is measured by light scatter using the percent transmittance of light (or absorbance) through the mixture of the media and assay compound. As measured on a spectrophotometer, the assay compound should have a background color at a concentration to be used in an assay of less than 1000, preferably less than 800, and most preferably less than 500 milliabsorbance units at 340 nanometers (25 C) blanked against distilled or deionized water. The assay compound will usually be used at a concentration of 0.5 to 10 mM. A useful concentration for determining solubility is 5 mM.

Preferably, a two fold excess quantity of the assay compound that will react with the enzyme during the time of the assay must be soluble in the aqueous media. An excess of assay compound is preferred. If an insufficient amount of the assay compound is provided, the enzyme reaction will completely hydrolyze the assay compound and the dynamic range of the assay will be limited. The resulting indicator compound will have a limited fluorescence duration. However, when an excess of the assay compound is employed, the enzyme reaction will continuously hydrolyze the assay compound and the fluorescence duration will continue during the enzyme reaction. This provides the advantage of having a longer time period in which to sense for one or more reaction states of the assay compound.

In addition, a solubilizing component can be utilized with the assay compound to assist the transfer of the assay compound into a metabolically active cell. The solubilizing component is present in an amount effective to enable the assay compound to pass through the cell lipid bilayer without detrimentally affecting the cell. The solubilizing component should be carefully chosen because the wrong solubilizing component can cause lysis or cell death.

When the assay compound has a background color (at the concentration to be used in an assay) greater than 1,000, greater than 800 or greater than 500 milliabsorbance units, a solubility component may be used to lower the background color to less than 1,000, less than 800 or less than 500 milliabsorbance units. However, the concentration of the solubilizing component is limited. If a high concentration of the solubilizing component is used, metabolically active cells will be lysed. If a low concentration of the solubilizing component is used, sufficient solubility of the assay compound will not be attained. The effective amount of solubilizing component may be empirically determined, but is typically less than 10.0% by weight of the assay compound.

Suitable solubilizing components include non-ionic surfactants, polyethylene glycol, dimethyl sulfoxide (DMSO), and mannitol. Commercially available solubilizing products include BRIJ 35 (polyoxyethylene lauryl ether) and TWEEN 20 (ethylene oxide with hydrophobic base from propylene oxide and propylene glycol) which are available from ICI Americas, Inc., and PLURONlC 25 R8 (ethylene oxide with hydrophobic base from propylene oxide and propylene glycol) which is available from BASF Wyandotte and TRITON X100 (octylphenoxy polyethoxy ethanol) which is available from Rohm and Haas Company. The preferred solubilizing component is DMSO.

The media in which the assay compound is dissolved must be compatible with the cell so that the cell can remain metabolically active in the media for at least the duration of the assay. The media is preferably sterile and free of endotoxin and chemicals that adversely affect the physiology of the cell. The assay compound is preferably completely soluble in the media at the concentration at which it is used. The assay compound is preferably used in concentrations up to the saturation or the suspension level or before turbidity occurs. The media may be physiological saline or a buffered solution (phosphate buffered saline) in which the assay compound and other additives are dissolved. The media should preferably include a buffer agent so that the pH of the assay mixture of metabolically active cells and assay compound is maintained at a point that is appropriate for the enzyme hydrolysis.

For storage purposes, the compound and media mixture should can be frozen or lyophilized, but preferably it will be lyophilized. Lyophilization should occur under conditions where sublimation of the solvent occurs upon application of a vacuum. Applying a vacuum to the sample at a temperature where a liquid forms on the solid before going to a gas phase, referred to as "melt back" may cause degradation of the compound. Appropriate temperatures should be determined for each compound, and preferred temperatures are usually −5° C. to −35° C. for predominantly aqueous solutions. During the thermal cycle of lyophilization, heat may be applied after sublimation to drive off any additional moisture. The product temperature should never exceed the heat applied and the product should be brought to room temperature over 15 to 72 hours. The vacuum should be returned to atmospheric conditions by bleeding in dry nitrogen. The product is stoppered at atmospheric pressure and temperature. The lyophilized compound is stored at 4° C. to 8° C. and may be reconstituted using endotoxin-free deionized water.

Auto-hydrolysis, which is the nonspecific hydrolysis of the substrate, yields cellular fluorescence not derived from the target enzyme. Stability of the substrate compound has been demonstrated to be a key factor in preventing auto-hydrolysis.

The assay compound and/or the assay reagent should be sufficiently stable so that no auto-fluorescence or chemiluminescence is created by the degradation of the assay compound prior to cleavage by the enzyme. Preferably, when the assay compound or assay reagent is stored at 20° C. for 30 days, preferably 90 days, more preferably 180 days and most preferably one year, the assay reagent exhibits a photon count of 100,000 or less. Photons can be measured by using a 2 millimolar solution of assay compound in deionized water and a path length of 1 cm against a rhodamine 110 standard as previously described. Fluorescent impurities should account for less than 10% of the fluorescence generated during the assay.

An acceptable assay reagent should have the following three characteristics: (1) there should be a low level of native free fluorescence that is absorbed by the cells, non-specifically. Thus, there should be a low level of fluorescent impurities. The acceptable and preferred levels of these impurities have already been described. (2) The reagent should be stable over time so that it does not need to be used shortly after it is prepared. Certain impurities and certain additives can increase the rate of autohydrolysis which increases the fluorescence of the reagent. Acceptable and preferred stabilities have already been discussed. (3) The reagent should also have a high enough rate of reaction with the enzyme being measured so that fluorescence generated as a result of reaction between the enzyme and the reagent can be easily measured. In one aspect, the reaction rate should be sufficiently high that fluorescence generated as a result of the reaction of the assay reagent and the targeted enzyme inside the cell is at least 2 times, preferably at least 10 times, more preferably at least 50 times and most preferably at least 100 times greater than other non-specific fluorescence generated in the assay.

V. Assay Conditions

The concentration of cells to be analyzed which are contained in a media should be high enough to provide a reading of the desired number of cells within the desired time period, taking into consideration the speed of the instrument that is being used. For current flow cytometry techniques, a concentration of about three million cells per milliliter is appropriate to yield a measurement of about 10,000–15,000 cells in about 1–2 minutes.

The assay compound is generally employed in concentrations in excess of the amount which can be completely hydrolyzed by the quantity of enzyme within the time of the assay. An assay compound concentration that is too high can have a negative affect on enzyme activity.

The assay compound concentration in a cellular optimization is determined using Km (a known rate constant) and $V_{MAX}$ (maximum velocity) calculations. The assay compound is preferably present in an amount from about 2 to about $100 \times V_{MAX}$ and most preferably from about 2 to about 10 times the amount which can be completely hydrolyzed by the enzyme within the duration of the assay period.

The assay may be conducted either as a rate determination or as an end point determination. Rate determinations are preferred, because they are generally less affected by auto-fluorescence. Consequently, a rate determination assay is more sensitive and precise. In a rate determination, the fluorescence of the assay compound-cell analyte mixture may be determined promptly after the cell analyte is contacted with the assay compound. The ability to see a signal and distinguish it from background noise determines the initial starting point of data collection and the final data point is preferably determined at the point where the slope of the reaction rate changes, typically more than 2%.

Most cellular reactions do not strictly obey zero-order kinetics. Most cellular enzymes show a delay between the time of exposure of the cells to the assay compound, and the ability to detect a signal that is greater than the background noise. Cellular enzymatic reactions that do not obey zero order kinetics are still useful measurements as first order, pseudo first order, or initial rate measurements. Multiple enzymes in a reaction (mixed reactions) are displayed by slope changes during the time course being monitored.

In an endpoint determination, the enzyme hydrolysis reaction is allowed to proceed for a predetermined length of time, usually at $V_{MAX}$. The reaction time can be calculated based on whether the reaction is zero order or first order kinetics using Michaelis—Menton methodology. Alternatively, the reaction time can also be adjusted by a different elapsed time for pseudo-first order reactions.

It has been determined that a number of factors will decrease the reliability of the assay, and yield false positive, or erroneous indications of enzymatic activity. These include (i) extended reaction between the cell analyte and the assay compound; (ii) another, non-targeted enzyme that is cleaving the leaving group; (iii) auto-hydrolysis of the assay compound; (iv) inhibitors or stimulators that are present and undetected; (v) cells that are no longer metabolically active, or dead; (vi) mixed populations of cells; (vii) a transfusion of the patient before sampling; (viii) non-specific dye uptake by negative cells; and (ix) background fluorescence. The creation of false negatives, or false indications of a lack of enzymatic activity, can be caused by (i) insufficient reaction between the cell analyte and the assay compound, (ii) a hypoosmotic media leading to a decrease in cell activity; (iii) a cell that is no longer metabolically active; (iv) burst cells; and (v) the presence of inhibitors to the target enzyme.

It has been further determined that assays will be significantly improved if reaction conditions are adjusted to maximize the activity of the assayed enzyme relative to other non-assayed enzymes which might otherwise compete for the leaving group. More specifically, the targeted enzyme can be involved in a chain cascade reaction of enzymes sequentially coupled to other enzymes, as in a multi-enzyme reaction cascade.

The reaction conditions can be adjusted to maximize the efficiency of the pathway, or to decrease the efficiency of competing pathways. Such conditions preferably include at least one of pH, choice of form of assay compound, temperature, osmotic pressure, ionic strength, and reaction time.

The pH at which an enzyme is most efficient will generally be between about 4 and 7.5. Preferably the pH of the assay compound will be pH 4.5 to 7.0, and most preferably from 4.7 to 6.7. The pH of the assay mixture is controlled by dissolving the cell analyte and assay compound in an appropriate buffer.

A reaction run using the same data collection window without the enzyme source will determine auto-hydrolysis of the substrate and therefore the potential for negative cells to absorb the dye non-specifically resulting in false positive.

The time of the assay is typically less than 30 minutes, preferably less than 20 minutes, usually between 5 seconds and 20 minutes, and most preferably between about 10 seconds and about 5 minutes. Some enzyme systems, such as esterases, can react with the assay compound in shorter periods of time due to concentrations of enzymes found in the cell. The reaction time should be limited so that the effects of cellular expulsion of the indicator compound will be avoided.

The temperature at which the assay is performed must be physiologically acceptable to the cell. The temperature must be high enough to retain viability and to ensure enzyme activity, but not so high as to cause degradation or other deleterious reactions involving the leaving group, the enzyme, or other components of the mixture. Particular enzymes, or enzymes in particular pathways, are more reactive at particular temperatures. The temperature is preferably maintained between about 30° C. to about 40° C., more preferably between about 35° C. and about 38° C., and most preferably between about 36° C. to about 38° C.

The osmotic pressure of the assay mixture is controlled to be within physiological ranges from about 250 milliosmoles to 350 milliosmoles, preferably from about 275 milliosmoles to 320 milliosmoles. The osmotic pressure must be selected to maintain the viability of the metabolically active whole cell. Variations in osmotic pressures will result in lysis of the cell, severe shrinking or shriveling (crenation) when too low, and swelling or bursting (stomatolysing) of the cell when too high.

The fluorescence reading is made after the reaction has occurred or after a specific period of time. Typically, the reaction is stopped by immersing the reaction container in ice and water which cools the cells to about 0° C. Sensing for one or more reaction states by fluorescence determinations confirms cleavage of the indicator group by the enzyme.

The fluorescence determinations can be performed on a Image Analysis System (IAS) or a Flow Cytometer (FC) or such other instruments which are capable of fluorescence determinations. The IAS is a microscope based system that measures fluorescence known to those skilled in the art. A representative example of an IAS is the Metamorph™ by Universal Imaging Corporation, West Chester, Pa. The structure and operation of flow cytometers is also well documented in the literature. Alternatives to traditional FC include slit-scan FC and stopped-flow FC. The type of instrument used to conduct the experiments described in the examples was a flow cytometer (for example, a Coulter Profile® flow cytometer manufactured by Coulter Corporation of Miami, Fla). This flow cytometer measures fluorescence across the entire cell. Flow cytometric methods which measure fluorescence in only a part of the cell, such as slit scan flow cytomeltry, have significant utility in the invention because the background fluorescence is significantly reduced when measurements are focused on the region of the cell where the enzyme is located.

The fluorescence determinations can also be taken by a spectrofluorometer which has the capability to measure the very low fluorescence levels that are generated by the assay. The spectrofluorometer is tuned to the excitation and emission wavelengths of the particular indicator being used. Preferred compounds such as rhodamine 110 and fluorescein have excitation and emission wavelengths of about 495 to 498 nm (excitation) and 520 to 525 nm, respectively. The Model 8000C photon counting spectrofluorometer manufactured by the SLM company, a subsidiary of Milton Roy (Chicago, Ill.) was used.

The flow cytometer can perform additional measurements in addition to a single wavelength fluorescence measurement. The flow cytometers can be equipped to measure fluorescence at two or more separate wavelengths. Such readings are useful to perform assays according to the invention when using more than one assay compound, or for using cell surface markers, such as monoclonal antibodies, to determine cell phenotype.

VI. Assay Protocols

Preferred sample preparations by which enzymes can be assayed using the reagents prepared according to the method of the invention have been developed. Examples of these sample preparations can be modified, and are included herein to disclose those procedures that are currently preferred. Sample preparation can be divided into four different processes represented by Examples 1, 2, 3 and 4 which are illustrated in FIGS. 1A, 1B, 1C and 1D, respectively. The choice of sample preparation is dependent upon the user and the analyte. The four processes are:

EXAMPLE 1

Examination Of Leukocytes Or Tissue Cells With Erythrocyte Contamination With Post- Lysing A sample, consisting of whole blood (in EDTA, Heparin or ACD) or dissociated tissue or body fluids (synovial fluid) or cell culture media is obtained and stored in a manner so as not to decrease viability. The sample is washed sufficiently to remove plasma, media, body fluid, debris and extra-cellular enzymes. The wash media consists of a physiologically balanced buffered salt solution. The washed cells are incubated at 37° C. 50 mL of sample and 25mL of substrate media are mixed together and allowed to incubate at 37° C. for a predetermined amount of time. At the end of the incubation period, unwanted cells are lysed with a lytic reagent, i.e., erythrocytes are removed. Compatible lytic systems are Q-Prep™, an acid lyse (formic acid/quench), Erythrolyse™, (acid lyse/detergent/quench) or hypotonic ammonium chloride. The sample is then measured for fluorescence. The referenced lytic systems are commercially available from Coulter Corporation, Miami, Fla.

EXAMPLE 2

Examination Of Leukocytes Or Tissue Cells With Erythrocyte Contamination With Pre- Lysing A sample, consisting of whole blood (in EDTA, Heparin or ACD) or dissociated tissue or body fluids (synovial fluid) or cell culture media is obtained and stored in a manner so as not to decrease viability. Unwanted cells, i.e. erythrocytes, are lysed with a lytic reagent. Compatible lytic systems are acid lysed (formic acid/quench), TVCS lyse (quaternary ammonium salts)/quench or hypotonic ammonium chloride. The sample is washed sufficiently to remove plasma, media, body fluid, debris and extra-cellular enzymes. The wash media consists of a physiologically balanced buffered salt solution. The washed cells are incubated at 37° C. 50 mL of sample and 25 mL of substrate media are mixed together and allowed to incubate at 37° for a predetermined amount of time. At the end of the incubation period, the sample is then measured for fluorescence.

EXAMPLE 3

Examination Of Platelets, Erythrocytes, Leukocytes, Dissociated Tissue, Body Fluids And Cell Culture Media A sample, consisting of whole blood (in EDTA, eparnn or ACD) or dissociated tissue or body fluids (synovial fluid) or cell culture media is obtained and stored in a manner so as not to decrease viability. The sample is washed sufficiently to remove plasma, media, body fluid, debris and extra-cellular enzymes. The wash media consists of a physiologically balanced buffered salt solution. The washed cells are incubated at 37° C. 50 mL of sample and 25 mL of substrate media are mixed together and allowed to incubate at 37° C. for a predetermined amount of time. At the end of the incubation period, the sample is then measured for fluorescence.

EXAMPLE 4

Examination Of Platelets, Erythrocytes, Leukocytes, Dissociated Tissue, Body Fluids And Cell Culture Media Using A Mechanical Separation To isolate A Cell Population A sample, consisting of whole blood (in EDTA, Heparin or ACD) or dissociated tissue or body fluids (synovial fluid) or cell culture media is obtained and stored in a manner so as not to decrease viability. A mechanical separation to isolate a specific cell population is performed, i.e., ficoll, differential centrifugation, differential precipitation. The sample is washed sufficiently to remove plasma, media, body fluid, debris and extra-cellular enzymes. The wash media consists of a physiologically balanced buffered salt solution. The washed cells are incubated at 37° C. 50 mL of sample and 25 mL of substrate media are mixed together and allowed to incubate at 37° C. for a predetermined amount of time. At the end of the incubation period, the sample is then measured for fluorescence.

The instruments used to detect fluorescence are the flow cytometer or fluorescent microscope. There are four different instrument configurations for the flow cytometer, A, B, C and D. Any of the four configurations can be used with any one of the sample preparations described above. The choice of which configuration is selected is dependent upon the user and the information sought to be obtained. The four configurations are:

Configuration A:

Configuration A analyzes the cells by size, granularity and single color. On the first configuration, the flow cytometer separates the cells by size and granularity. The activity of an enzyme is then assayed using the reagent compound. Two samples are allowed to proceed at different times and the reaction is stopped. The difference in fluorescence permits the calculation of a rate. Total population counts preferred are 500 to 500,000 cells. Use. of light scatter or hematology parameters provide size and granularity separation. Intensity bitmap of desired populations and determination of fluorescent activity by single measurement point or multi-point measurement can be employed. Determine count, percentage and fluorescent intensity of a multi-modal population representing enzymatic activity.

Configuration B:

Configuration B analyzes the cells by size, granularity and two colors. In the second configuration, the flow cytometer separates the cells by size and granularity. Cell morphology is determined by a fluorescence assay with a monoclonal antibody marker. The rate of the hydrolysis of the assay compound is then determined. Total population counts preferred are 500 to 500,000 cells. Use of light scatter or hematology parameters provide size and granularity separation. Intensity bitmap of desired populations and determination of fluorescent activity by single measurement or multi-point measurement can be employed. Determine count, percentage and fluorescent intensity of a multirnodal population representing enzymatic activity. The analysis is a 2-color analysis measuring enzymatic activity in one color and surface-marker antibody cell morphology in the other color.

Configuration C:

Configuration C analyzes the cells by size, granularity, two colors and backgate fluorescence. Configuration 3 is a modification of the Duque method. Duque, R. E., "Flow Cytometric Analysis of Lymphomas and Acute Leukemias", *Annals of the New York Academy of Sciences, Clinical Flow Cytometry*, 677, pp. 309–325 (Mar. 20, 1993). The size and granularity of the cell are separated by a flow cytometer using light scatter and/or with surface markers, such as monoclonal antibodies. A series of cell populations are determined, with rearrangement of the histogram to identify the disease and normal cells. The activity of the enzyme is then assayed. Total population counts preferred are 500 to 500,000 cells. Use of light scatter or hematology parameters provide size and granularity separation. Intensity bitmap of desired populations and determination of fluorescent activity by single measurement point or multi-point measurement can be employed. Determine count, percentage and fluorescent intensity of a multi-modal population representing enzymatic activity. The analysis is a 2-color analysis measuring enzymatic activity in one color and surface-marker antibody cell morphology in the other color. Backgate fluorescence data on size and granularity to determine count and percent of diseased cells.

Configuration D:

Configuration D analyzes activity of a population of cells over time. Total population counts preferred are 500 to 500,000. Use of light scatter or hematology parameters provide size and granularity separation. Intensity bitmap of desired populations and determination of fluorescent activity by single measurement point or multi-point measurement can be employed. Determine count, percentage and fluorescent intensity of a multi-modal population representing enzymatic activity. The analysis is a 2-color analysis measuring enzymatic activity in one color and surface-marker antibody cell morphology in the other color.

VII. Data Analysis

Examining blast cell positions in a histogram using forward and side scatter light scatter indicates that a majority of the blast cells co-localize with lymphocyte and monocyte cells, but primarily with the lymphocyte cells.

It has been further found that normal lymphocyte enzymatic levels are different when compared to blast cells providing the opportunity to separate normal lymphatic cells from blast cells by this invention. In addition, it has been determined that a panel of enzymes can be employed to determine blast cell lineage.

Blast cells may be of lymphocytic, monocytic or granulocytic origin. For example, those that are of granulocytic and monocytic origin have large quantities of oxidoreductase enzyme activity, resulting from NADPH oxidase and myeloperoxidase, within the cell. Therefore, exposing the cell sample to an assay reagent to identify the oxidoreductase enzyme activity and bit mapping the lymphocytic area results in a fluorescent histogram that is bimodal when both normal lymphocytes and blast of granulocytic or monocytic lineage are present.

Further exposing the cell sample to assay reagents used to measure esterase enzyme activity results in fluorescent histograms which enables determination of monoblast or myeloblasts. More specifically, when the results of the two assay reagents used to measure esterase activity result in fluorescence histograms having fluorescence mean channel ranges which are of different intensities, it indicates the presence of monoblast cells. However, when the results of the two assay reagents used to measure esterase activity results in fluorescence histograms having fluorescence mean channel ranges which are of equal fluorescence mean channel range, indicates the presence of myeloblast cells.

At least three patterns of data may be apparent; all cells have a low intensity of fluorescence in the histogram, all cells have a high intensity of fluorescence in the histogram, or a bimodal distribution will be present in the fluorescent histogram. In a bimodal histogram, the percent blast cells can be determined by taking a fluorescent count in a chosen region wherein the blast cells reside and divide by a total count of the leukocytes in the leukocyte bitmap region from the FS and SS histogram times 100. Determination of percent blast cells obtained by flow cytometry with the assay compound correlate to the percent blast cells obtained by the Wright stain method. This is shown by FIG. 2 which shows a correlation between Wright's stain versus the method of this invention. In a similar way, the use of light scatter properties and the assay reagents 3', 6' fluorescein dibutyrate (FDB), 3', 6' fluorescein dichloroacetate (FDClAc), fluorescein-β-D-diglucoronide, 3', 6' fluorescein diacetate (FDA), 3', 6' fluorescein diacetate.soduim fluoride (FDA-NaF), and 3', 6' fluorescein diphosphate.ammonium salt (FDP-AS) can be used to distinguish blast cells by fluorescence enzyme activity by comparison within the panel to further differentiate malignant cells.

The measured fluorescence intensity can be converted from fluorescence mean channel (in peak or integrated mode) to MESF (molecules of equivalent soluble fluorochrome, Flow Cytometry Standards Corp., San Juan, P.R.) or International Units of hydrolysis per cell.

The following detailed Examples are intended to illustrate this invention, but not limit its scope.

EXAMPLE 5

Determination of Monoblast Cells

A. MATERIALS REQUIRED
1) 1× Hanks Balanced Salt Solution (HBSS) (See INTERFERING SUBSTANCES No. 1), pH 7.40–7.55, no sodium bicarbonate
2) Phosphate Buffered Saline* (PBS), pH 7.00–7.55, pyrogen free
3) Pipettes
4) Pipette tips
5) Glass tubes (12×75 mm borosilicate)
6) 37° C. water bath
7) Crushed ice
8) Q-Prep and reagents (Coulter Corporation)
9) Pyrogen-free water
10) COULTER EPICS® flow cytometry system
11) Centrifuge
12) Assay reagents used to identify esterase enzyme activity
   a. DCFH-DA (3', 6' fluorescein dichloroacetate)
   b. FDA (3', 6' fluorescein diacetate)
   c. FDA-NaF (3', 6' fluorescein diacetate sodium fluoride)
   d. FDClAc (3', 6' fluorescein dichloroacetate)
   e. FDB (3', 6' fluorescein dibutyrate)

B. PROCEDURE
1) Instrument Set Up: Verify the fluidic integrity of the EPICS XL flow cytometry system (or equivalent) using Flow-Check™ Fluorospheres (Coulter Corporation). For consistent results, the high voltage must be set daily using a fluorosphere standard. For example: analysis of a washed whole blood sample, set your LFL1 high voltage to place Flow-Set™ Fluorospheres (Coulter Corporation) into the target mean channel 22.7±0.30 of your fluorescence histogram. Use this high voltage to analyze the assay reagents having the same target mean channel requirements. For FDClAc and FDB use high voltage to place Flow-Set fluorospheres into the target mean channel 6.0±0.1. Each day reestablish the high voltage required to place the standard fluorosphere into the same target channel. When changing to a new lot of Flow-Set fluorospheres, compare the current lot with the new lot to establish new mean target values.

2) Sample Preparation: Check the pH of the HBSS and the PBS daily. Adjust buffers to a pH of 7.40–7.55. Wash samples in either HBSS or PBS (10:1). Spin samples at 200 g for 10 minutes. Repeat the wash procedure twice. The second and third washes for whole-blood samples can be spun at 500±200 g for 5 minutes.

3) Gently resuspend the cell pellet in either HBSS or PBS to a cell concentration of $3.0\pm0.5\times10^6$ cells/mL. Do not vortex.

4) Label 12×75 mm glass test tube(s) with the appropriate assay reagent name. Label one blank tube per sample. Add 50 μL of the washed sample to each of the labeled tubes.

5) Procedure: Place the tubes into a 37° C. water bath for 5–10 minutes. Once samples are warmed you must proceed through analysis. Prepared tubes must be analyzed within 30 minutes of incubation with the assay reagent as defined in step 7.

6) Just prior to use, reconstitute the assay reagent if in lyophilized form.

7) Maintain a 37° C. reaction temperature by leaving the prewarmed sample tube(s) in the water bath during the addition of the assay reagent. Add 25 μL of HBSS or PBS to the blank tube. Add 25 μL of the assay reagent to the appropriate labeled tube(s).

Note: Assay reagent(s) should be added to the tubes in the water bath at intervals of approximately 15 seconds to maintain precise incubation times for each tube.

Quickly mix by hand after each addition. Return the tube to the water bath and incubate DCFH-DA, FDA, and FDA-NaF at 37° C. for an equal period of time for each assay reagent. The period of time for these assay reagents can be from 2 to 10 minutes, preferably for 4 to 6 minutes. In this example, each assay reagent was incubated for 5 minutes. For FDClAc and FDB assay reagents incubate at 37° C. for an equal period of time for each assay reagent. The period of time for these assay reagents can be from 15 seconds to 2 minutes, preferably for 30 to 90 seconds. In this example, each assay reagent was incubated for 60 seconds.

Remove each tube at the completion of its incubation time and place on crushed ice for a minimum of 3 minutes. Tubes should remain on ice until ready to proceed to steps 8 and 9. These tubes can be held on ice for up to 20 minutes.

Immediately proceed from the crushed ice to steps 8 and 9 for each tube. (For consistency, each tube should be removed at the same time interval as the assay reagent addition in both 37° C. and ice incubation steps.)

8) For a washed whole-blood sample, process the tubes on a Q-Prep Workstation instrument (Coulter Corporation). Follow Q-Prep procedures and guidelines for preparing whole-blood samples. For samples other than whole blood, suspend cells in 1 mL of cold HBSS or PBS.

9) Prepared tubes should be placed immediately on ice until analyzed.

10) To analyze, establish a scatter pattern [Forward Scatter (FS) vs. Side Scatter (SS)], and gate on the population(s) of interest. Verify that the scatter pattern is representative of the sample being analyzed. For example, expect to receive a typical three population scatter pattern for a normal whole blood prep. Adjust the threshold, forward scatter gain, and side scatter high voltage to make the three part differential evident. Determine the mean fluorescent intensity of the populations of interest by using the high voltage established in step 1. The blank is used only as a guideline to ensure that positive fluorescence appears higher in mean channel than the blank.

C. RESULTS

In this example the monoblast cells co-localize within the lymphocyte bitmap, and show a higher fluorescence mean channel range than the lymphocytes with DCFH-DA assay reagent. When the results of the FDA and FDA-NaF assay reagents are compare to each other, a decrease fluorescence mean channel range is shown in the FDA-NaF esterase assay. The FDClAc and FDB esterase assays show fluorescence mean channel range proportional to enzyme activity. If the sample has monoblast, then the FDB assay will have a fluorescence mean channel range greater than a fluorescence mean channel range of the lymphocyte cells in the cell sample. The FDClAc assay will have a fluorescence mean channel range that would be lower than or equal to the lymphocyte cells in the cell sample.

Using Wright's stain and a 400 count differential indicates that there are blast cells present.

D. INTERFERING SUBSTANCES

1) Pyrogens found in distilled water may activate cells of the immune system, altering enzymatic activity. Always use pyrogen-free water, buffers and materials.
2) CellProbe Reagents are formulated to be hydrolyzed by specific enzymes. However, cells contain other enzymes that may compete for hydrolysis of the enzyme substrate. Inhibitors may be added to further enhance specificity. Red cell lysates and platelets may affect enzyme activity of WBC populations.
3) Whole-blood samples can be collected in Heparin, EDTA or ACD and should be processed within 6 hours of collection. Choice of anticoagulant should be considered in enzyme assays. For example, EDTA chelates metal ions such as zinc, calcium and magnesium which may affect proteolytic activity of some enzymes.
4) Mononuclear separations and tissue preparation techniques may activate cellular enzymes, changing acquired results. Avoid the use of enzymatic digestion in solid tissue preparations.
5) Viable cell preparations provide the most accurate measure of cellular enzyme activity. Nonviable cell populations can be analyzed but may provide different levels of activity than viable cells. Mixed populations of viable and nonviable cells are not recommended as they will skew the final results.

EXAMPLE 6

Determination of Myeloblast Cells

The material and procedure of Example 5 is repeated. However, the results are different. In this example the myeloblast cells co-localize within the lymphocyte bitmap, and show a higher fluorescence mean channel range than the lymphocytes with DCFH-DA assay reagent. When FDA and FDA-NaF assay reagents are compare to each other, the same or approximately the same fluorescence mean channel range is shown. The FDClAc and FDB esterase assays show fluorescence mean channel range proportional to enzyme activity. If the sample has myeloblasts, then the FDB assay will have a fluorescence mean channel range less than or equal to a fluorescence mean channel range of the lymphocyte cells in the cell sample. The FDClAc assay will have a fluorescence mean channel range that would be greater than the lymphocyte cells in the cell sample.

FIG. 3A contains bitmap 1 which is the FS, SS region of lymphocytes and blast cells. FIG. 3B is a fluorescence histogram of bitmap 1 showing a bimodial fluorescence distribution with DCFH-DA assay reagent. Using Wright's stain and a 400 count differential indicates that there are 17% blast cells. By the using this invention and counting approximately 5,000 leukocytes, it was determined that 21.6% blast cells were present. FIG. 2 depicts identification of percent myeloblast cells using the method of this invention and a correlation to a Wright's stain determination of percent blast cells.

EXAMPLE 7

Determination of Lymphoblast Cells

The materials of Example 5 are repeated except that the assay reagents used in this example comprise DCFH-DA, FDB, FDP-AS, and fluorescein-β-D-diglucoronide. The procedure of Example 5 is repeated except that when using FDP-AS and fluorescein-β-D-diglucoronide one should use high voltage to place Flow-Set fluorospheres into the target mean channel 22.7±0.30 and in step 7, the incubation time should be an equal period of time for each assay reagent. The period of time for these assay reagents can be from 5 to 15 minutes, preferably for 8 to 12 minutes. In this example, each assay reagent was incubated for 10 minutes.

In this example, the lymphoblast cells co-localize within the lymphocyte bitmap, and show a fluorescence mean channel range which is approximately equal to the fluorescence mean channel range of the lymphocytes with DCFH-DA assay reagent. The FDB and fluorescein-β-D-diglucoronide assays when compared to lymphocytes show a bimodal distribution where the blast cells have a fluorescence mean channel range which is lower than the fluorescence mean channel range of the lymphocyte cells in the cell sample. The FDP-AS esterase assay shows a fluorescence mean channel range proportional to enzyme activity. If the sample has lymphoblasts, and the FDP-AS assay has a fluorescence mean channel range lower than the fluorescence mean channel range of the lymphocyte cells in the cell sample, then it is a non T-cell.

Figure 4A:
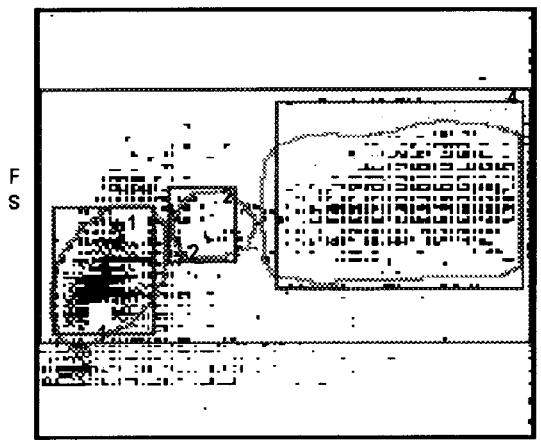
FIGS. 4A and 4B depict histograms of lymphocytes, monocytes, granulocytes and blast cells which illustrates the use of an assay reagent according to this invention to provide an indication that the blast cells are not myeloblast cells.
Figure 4B:
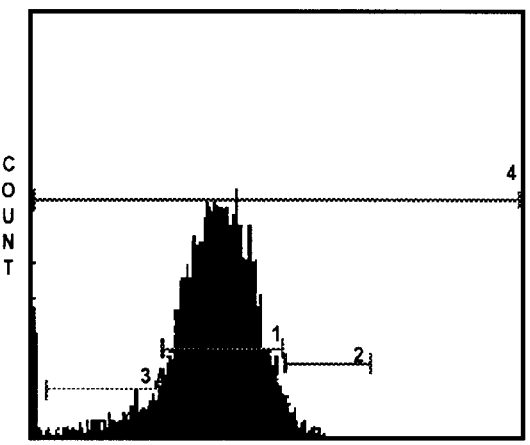

FIG. 4A contains bitmap 1 which is the FS, SS region of lymphocytes and blast cells. FIG. 4B is a fluorescence histogram of bitmap 1 showing a unimodal fluorescence distribution with DCFH-DA assay reagent. The unimodal fluorescence histogram indicates that the blast cells are not myeioblast. FIG. 5A contains bitmap 1 which is the FS, SS region of lymphocytes and blast cells. FIG. 5B is a fluorescence histogram of bitmap 1 showing a bimodal fluorescence distribution with FDB assay compound. The bimodal fluorescence histogram indicates that the blast cells are lymphocytic blast cells.

The identity of lymphoblast cells was confirmed by fluorescence microscopy. Using Wright's stain and a 400 count differential indicates that there are 34% blast cells. By using this invention and counting approximately 5,000 leukocytes, it was determined that 38% blast cells were present.

The results of this invention demonstrate the ability to resolve cell types based on their enzymatic activity.

All patents and publications referred to in this application are hereby incorporated by reference in their entirety.

The invention has been described with reference to the preferred embodiments. It should be understood, however, that the invention is not so limited, and the scope of the invention should be determined with reference to the following claims, rather than to the foregoing specification.

We claim:

1. A method for identification of blast cells in a fluid sample comprising:
   a) taking a body fluid sample from an individual, said sample containing metabolically active cells,
   b) preparing said fluid sample to form at least one test sample, said test sample containing metabolically active cells,
   c) adding an assay reagent to each prepared test sample to form a test cell mixture, said assay reagent containing a fluorogenic indicator group being selected for its ability to have a non-fluorescent first state before said assay reagent reacts with an enzyme within said cells, and a fluorescent second state excitable at a wavelength above 450 nm after said assay reagent reacts with said enzyme within said cell, said assay reagent having a fluorescence less than the auto-fluorescence of a metabolically active cell before reacting with said enzyme within said cell,
   d) illuminating said test cell mixture with a beam of light which causes said light to be scattered and exciting said test cell mixture with a fluorescent wavelength above 450 nm which causes said test cell mixture to have a fluorescent second state,
   e) detecting fluorescence and light scatter of the cells in said test cell mixture, and
   f) correlating said fluorescence and said light scattering of said cells to identify blast cells contained is said test cell mixture.

2. The method of claim 1, wherein said assay reagent reacts with an oxidoreductase enzyme.

3. The method of claim 2, wherein the assay reagent is selected from dicholorofluorescin diacetate (DCFH-DA), dihydrorhodamine 123 (DHR 123), and nitroblue tetrazolium.

4. The method of claim 3, wherein the assay reagent is DCFH-DA.

5. The method of claim 1, wherein said fluid sample is used to prepare at least two test samples, wherein a first test sample is added to a first assay reagent which reacts with oxidoreductase enzymes, and a second test sample is added to a second assay reagent which reacts with an esterase enzyme.

6. The method of claim 5, wherein the first assay reagent is selected from DCFH-DA, DHR 123, and nitroblue tetrazolium.

7. The method of claim 6, wherein the first assay reagent is DCFH-DA.

8. The method of claim 5, wherein the second assay reagent is fluorescein dibutyrate (FDB).

9. The method of claim 5, wherein said detecting of fluorescence for the cells in said test sample for oxidoreductase enzymes activity results in a histogram having a unimodal fluorescence mean channel and detecting of fluorescence for the cells in said test sample for esterase enzyme activity results in a histogram having a bimodal fluorescence mean channels.

10. The method of claim 9, wherein the blast cells are lymphoblast cells.

11. The method of claim 1, wherein said fluid sample is used to prepare at least three test samples, wherein a first test sample is added to a first assay reagent which reacts with a peroxidase enzyme, a second test sample is added to a second assay reagent which reacts with an esterase enzyme, and a third test sample is added to a third assay reagent, said third assay reagent containing an inhibitor which inhibits enzyme activity of cells of monocytic lineage, and said third assay reagent reacts with said esterase enzyme.

12. The method of claim 11, wherein the first assay reagent is selected from DCFH-DA, DHR 123, and nitroblue tetrazolium.

13. The method of claim 12, wherein the first assay reagent is DCFH-DA.

14. The method of claim 12, wherein the second and third assay reagent is fluorescein diacetate (FDA).

15. The method of claim 14, wherein said inhibitor contained in said third assay reagent is sodium fluoride.

16. The method of claim 14, wherein the identity of the blast cells are monoblast cells.

17. The method of claim 14, wherein the identity of the blast cells are myeloblast cells.

18. The method of claim 1, wherein said fluid sample is used to prepare at least four test samples, wherein a first test sample is added to a first assay reagent which reacts with a oxidoreductase enzymes, a second test sample is added to a second assay reagent which reacts with an esterase enzyme, a third test sample is added to a third assay reagent which reacts with a phosphatase enzyme and a fourth test sample is added to a fourth assay reagent which reacts with a glucuronidase enzyme.

19. The method of claim 18, wherein the first assay reagent is selected from DCFH-DA, DHR 123, and nitroblue tetrazolium.

20. The method of claim 19, wherein the first assay reagent is DCFH-DA.

21. The method of claim 18, wherein the first assay reagent is selected from DCFH-DA, DHR 123, and nitroblue tetrazolium, and the second assay reagent is selected from FDA, fluoresein diacetate—sodium flouride (FDA-NaF), fluorescein dichloroacetate (FDClAc) and FDB.

22. The method of claims 5, 11 or 18, wherein said light scatter comprise forward angle light scatter and side scatter.

23. The method of claims 5, 11 or 18, wherein said detecting of said fluorescence occurs less than 20 minutes after adding said assay reagent to said test sample.

24. The method of claims 5, 11 or 18, which further comprises lysing erythrocytes from said body fluid.

25. The method of claims 5, 11 or 18, wherein said cells comprise lymphocyte and monocyte cells.

26. The method of claims 5, 11 or 18, wherein said body fluid is selected from a cell suspension prepared from lymph nodes, bone marrow and blood.

27. The method of claims 5, 11 or 18, wherein each assay reagent has a pH of approximately 4 to 7.5.

28. An assay reagent for identification of blast cells in a fluid sample by measurements of cellular enzyme activity comprising:
   a) an assay compound selected from 3', 6' fluorescein dichloroacetate and 3', 6' fluorescein dibutyrate; and
   b) a physiological buffer, wherein said assay reagent has a fluorescence less than autofluorescence of a metabolically active cell before reacting with an enzyme within a cell and a pH from 4 to 7.5.

29. The assay reagent of claim 28, wherein said buffer is selected from selected from 2-N-morpholinoethanesulfonic acid (MES), N-tris(hydrovmethyl)methyl-2-aminoethanesulfonic acid (TES), 4-(2-hydroxyethel)-1-piperazineethane-sulfonic acid (HEPES) and Hanks Balanced Salt Solution (HBSS).

30. The assay reagent of claim 29, wherein said buffer is MES.

31. The assay reagent of claim 28, wherein said assay reagent is lyophilized.

32. The lyophilized assay reagent of claim 31, said assay reagent has a solubility less than 1000 milliabsorbance units.

33. The lyophilized assay reagent of claim 31, wherein said assay compound is 3', 6' flurescein dichloroacetate.

34. The lyophilized assay reagent of claim 31, wherein said assay compound is 3', 6' fluorescein dibutyrate.

* * * * *